(12) United States Patent
Ketelson et al.

(10) Patent No.: US 11,730,699 B2
(45) Date of Patent: *Aug. 22, 2023

(54) LIPID-BASED OPHTHALMIC EMULSION

(71) Applicant: Alcon Inc., Fribourg (CH)

(72) Inventors: Howard Allen Ketelson, Dallas, TX (US); James W. Davis, Falmouth, ME (US); Rekha Rangarajan, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 278 days.

This patent is subject to a terminal disclaimer.

(21) Appl. No.: 17/147,007

(22) Filed: Jan. 12, 2021

(65) Prior Publication Data

US 2021/0128468 A1 May 6, 2021

Related U.S. Application Data

(63) Continuation of application No. 16/281,316, filed on Feb. 21, 2019, now Pat. No. 10,925,892.

(60) Provisional application No. 62/633,359, filed on Feb. 21, 2018.

(51) Int. Cl.
| | |
|---|---|
| *A61K 31/736* | (2006.01) |
| *A61P 27/02* | (2006.01) |
| *A61K 9/00* | (2006.01) |
| *A61K 9/107* | (2006.01) |
| *A61K 47/14* | (2017.01) |
| *A61K 47/24* | (2006.01) |
| *B01F 17/00* | (2006.01) |
| *A61K 47/02* | (2006.01) |
| *A61K 47/10* | (2017.01) |
| *A61K 47/26* | (2006.01) |
| *A61K 47/34* | (2017.01) |
| *A61K 47/36* | (2006.01) |
| *B82Y 5/00* | (2011.01) |

(52) U.S. Cl.
CPC .......... *A61K 9/1075* (2013.01); *A61K 9/0048* (2013.01); *A61K 47/02* (2013.01); *A61K 47/24* (2013.01); *A61K 47/26* (2013.01); *A61K 47/34* (2013.01); *A61K 47/36* (2013.01); *B82Y 5/00* (2013.01)

(58) Field of Classification Search
CPC ...... A61K 9/1075; A61K 47/02; A61K 47/24; A61K 9/0048; A61K 47/26; A61K 47/34; A61K 47/36; B82Y 5/00
See application file for complete search history.

(56) References Cited

FOREIGN PATENT DOCUMENTS

| | | |
|---|---|---|
| CN | 102395274 A | 3/2012 |
| CN | 102525887 A | 7/2012 |
| CN | 107485602 A | 12/2017 |
| JP | 2011518842 A | 6/2011 |
| JP | 2013512912 A | 4/2013 |
| JP | 2013512917 A | 4/2013 |
| WO | 2010093992 A1 | 8/2010 |

OTHER PUBLICATIONS

Guzey, Mustafa, et al., "The effect of lubricating eye drop containing hydroxypropyl guar on perimetry results of patients with glaucoma and trachomatous dry eye", Ophthalmologica, 224, 2, 2009, pp. 109-115.
Labetoulle, Marc, et al., "Safety and efficacy of a hydroxypropyl guar/polyethylene glycol/propylene glycol-based lubricant eyedrop in patients with dry eye", British Journal of Ophthalmology, 101, 4, pp. 487-492.
Lane et al. "An Evaluation of the In Vivo Retention Time of a Novel Artificial Tear as Compared to a Placebo Control," Poster Presentation, Association for Research in Vision and Ophthalmology Annual Meeting (ARVO) 2009.
Mafi, Roozbeh, et al., "On formulating ophthalmic emulsions", Colloids and Surfaces B: Biointerfaces, 122, 2014, pp. 7-11.
Mafi, Roozbeh, "Novel guar crosslinkers for improved ophthalmic solutions", PhD dissertation available online on https://macsphere.mcmaster.ca/handle/11375/16805.
Mudgil, Deepak et al., "Guar gum: processing, properties and food applications—a review", Journal of food science and technology, 51 (3), pp. 409-418, Mar. 2014.
Petricek, Igor, et al. "Hydroxypropyl-guar gellable lubricant eye drops for dry eye treatment", Expert Opinion on Pharmacotherapy, 9, 8, pp. 1431-1436.
Rangarajan, Rekha, et al., "Effects of a hyaluronic acid/hydroxypropyl guar artificial tear solution on protection, recovery, and lubricity in models of corneal epithelium", Journal of Ocular Pharmacology and Therapeutics, 31/8, (2015), 491-497.

*Primary Examiner* — Shirley V Gembeh
(74) *Attorney, Agent, or Firm* — Sheng-Hsin Hu

(57) ABSTRACT

The present invention is directed to a lipid-based ophthalmic emulsion. The emulsion has an increased amount of a mucoadhesive galactomannan polymer that promotes a long-lasting protection against desiccation and moisture retention.

16 Claims, 3 Drawing Sheets

LIPID-BASED OPHTHALMIC EMULSION

This application is a continuation of U.S. patent application Ser. No. 16/281,316 filed 21 Feb. 2019; which claims the benefit under 35 USC § 119 (e) of U.S. provisional application No. 62/633,359 filed 21 Feb. 2018, incorporated by reference in its entirety.

TECHNICAL FIELD OF THE INVENTION

The present invention is directed to a lipid-based ophthalmic emulsion. More particularly, the present invention is directed to a lipid-based ophthalmic emulsion containing the gellable polymer hydroxypropyl guar and anionic lipids for improving desication protection and retention.

BACKGROUND OF THE INVENTION

Integrity of the tear film is essential for ocular surface homeostasis and functioning. Dry eye disease is a multifactorial condition characterized by tear film instability, and results in ocular discomfort and visual disturbance, severely impacting patient's quality of life. The outermost lipid layer of the tear film, formed by the meibum, helps to maintain tear film stability by reducing the rate of tear evaporation. Alteration in the tear lipid layer due to impaired quality or quantity of the meibum, is one of the most common cause of evaporative dry eye disease. Topically administered artificial tear substitutes/lubricant eye drops are the mainstay in the management of all types of dry eye disease and alleviate the symptoms and signs in patients with dry eye.

Chronic dry eye can lead to desiccation and damage of ocular surface tissues and disrupted epithelial cell barrier function. Installation of lubricating artificial tears that replenish moisture and decrease friction is a primary approach to dry eye management. Artificial tear compositions comprise compounds that lubricate and protect the ocular surface. In the context of dry eye disorders, artificial tear compositions can prevent symptoms such as pain and discomfort and can prevent bioadhesion and tissue damage induced by friction. A large number of potential compounds are available that are useful as lubricants and ocular surface protectants. For example, certain marketed artificial tear products contain natural polymers such as galactomannans. Other lubricants and ocular surface protectants include, for example, carboxymethylcellulose, glucomannan, glycerol, and hydroxypropylmethylcellulose. Though existing artificial tear compositions have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive, often leading to patient compliance issues. Furthermore, an ophthalmic emulsion containing the polymer hydroxypropyl guar, oil and anionic lipids may form oil globules on the surface of the eye. These globules are likely to result in blurring on instillation.

There is still a need to develop longer-acting formulations that reduce blurring on instillation and provide increased ocular hydration protection against desiccation and surface hydration.

SUMMARY OF THE INVENTION

The present invention is directed to an ophthalmic emulsion, the emulsion comprising:
water forming an aqueous phase;
oil forming an oil phase;
a hydrophilic surfactant having an HLB value from 10 to 18;
a hydrophobic surfactant having an HLB value from 1 to 6;
a charged phospholipid;
borate;
a mucoadhesive galactomannan polymer; and
a preservative;
wherein the mucoadhesive galactomannan polymer is present in the emulsion at a concentration of at least about 0.1 w/v % but no greater than 0.5 w/v %;
wherein the preservative is substantially free of a benzalkonium chloride; and
wherein the ophthalmic emulsion has a hydration protection against desiccation of at least 10% higher than a control emulsion, wherein the control emulsion has the same composition of the ophthalmic emulsion except of containing 0.05 w/v % of the same galactomannan polymer used in the ophthalmic emulsion.

BRIEF DESCRIPTION OF THE DRAWINGS

A more complete understanding of the present invention and the advantages thereof may be acquired by referring to the following description, taken in conjunction with the figures of the accompanying drawing in which like reference numbers indicate like features and wherein.

DETAILED DESCRIPTION OF THE INVENTION

Figure 1:
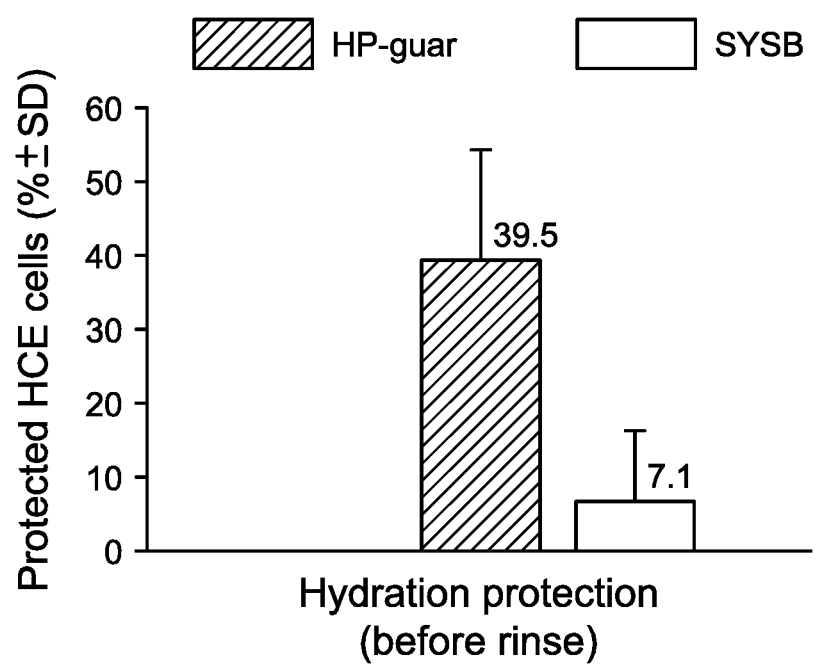
FIG. 1 is a bar chart comparing desiccation performance of a composition comprising 0.05% hydroxypropyl guar and 0.15% hydroxypropyl guar.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. The nomenclature used herein and the laboratory procedures described below are those well known and commonly employed in the art.

As used herein "droplet size $D_{90}$" refers to the droplet diameter corresponding to 90% of the cumulative undersize distribution by volume, i.e. 90 percent of the distribution lies below the D90. According to the present invention, particle or droplet size analyzers are used to determine emulsion oil droplet size. The Microtrac S3500 Particle Size Analyzer (Software Version 10.3.1) is a tri-laser particle size analyzer that can be used to measure emulsion oil droplet size. That particular analyzer measures laser light diffracted (scattered)

from particles (e.g., droplets) in a flowing stream. The intensity and direction of the scattered light is measured by two optical detectors. Mathematical analysis of the diffraction pattern by the software generates a volume distribution of droplet size. The droplet diameter corresponding to 90% of the cumulative undersize distribution by volume is used.

As used herein "percent of hydration protection against desiccation" refers to a mean value (with sample size n at least 20) of % cell viability after desication in cultured human corneal epithelial (HCE) cells pretreated with test formulations. According to the present invention, monolayer FTT (14-3-3) human corneal epithelial (HCE) cells were grown to confluence on collagen IV coated 48-well plates in EpiLife® medium containing calcium and supplemented with human corneal growth supplement for ~48 hours. Cells were then incubated with 150 μL test formulation (HP-guar emulsion, or SYSB) for 30 minutes at 37° C. To measure the cell hydration protection against desiccation, the test formulations were removed gently, and the cells were desiccated at 37° C. and 45% relative humidity for 30 minutes. To measure the hydration retention after desiccation, the test formulations were removed gently and the cells were rinsed three times with media (EpiLife® medium with calcium) and then desiccated as described above.

After desiccation, cell viability was measured using MTS assay (Promega, Madison, Wis., USA). The % viability was calculated relative to the undesiccated media control (Absorbance of test sample/Absorbance of the undesiccated media control×100). The protection (%) was calculated as the viability of the test formulation relative to the desiccated media control (% viability of the test sample−% viability of the desiccated media control).

The present invention is directed to an ophthalmic emulsion. The emulsions of the present invention are two phase systems comprising oil droplets dispersed in water. The droplet size $D_{90}$ is typically less than 700 nm but typically greater than 10 nm. Maintaining such droplet size is difficult since emulsions are typically thermodynamically or otherwise unstable and require one or more excipients to impart stability to the emulsion and prevent the oil droplets from coalescing. De-emulsification of the emulsions needs to be kinetically hindered particularly under exacerbated conditions such as storage of the emulsion at high ambient temperatures (e.g., warehouses during summer months, especially in tropical or central continental or Mediterranean climates), or by a temperature cycle in which the formulations are subjected to cyclical heating and cooling. Additionally, the presence of high ionic strengths in the aqueous phase can lead to de-emulsification.

While small droplet size is difficult to maintain for a simple emulsion, droplet size maintenance can be substantially more complicated when additional ingredients are included in the emulsion (see Surface properties and emulsification activity of galactomannans, Food Hydrocolloids, Volume 8, Issue 2, May 1994, Pages 155-173 Nissim Garti, Dov Reichman). For ophthalmic emulsions, it can be particularly difficult to integrate mucoadhesive materials, particularly mucoadhesive polymers, into the emulsion without causing undesirable instability in emulsion oil droplet size. It would be desirable to provide an emulsion that can maintain small droplets and it would be particularly desirable to be able to maintain small droplets in the presence of a mucoadhesive polymer.

The present invention is directed to an ophthalmic emulsion, the emulsion comprising:
water forming an aqueous phase;
oil forming an oil phase;
a hydrophilic surfactant having an HLB value from 10 to 18;
a hydrophobic surfactant having an HLB value from 1 to 6;
a charged phospholipid;
borate;
a mucoadhesive galactomannan polymer; and
a preservative;
wherein the mucoadhesive galactomannan polymer is present in the emulsion at a concentration of at least about 0.1 w/v % but no greater than 0.5 w/v %;
wherein the preservative is substantially free of a benzalkonium chloride; and
wherein the ophthalmic emulsion has a hydration protection against desiccation of at least 10% higher than a control emulsion, wherein the control emulsion has the same composition of the ophthalmic emulsion except of containing 0.05 w/v % of the same galactomannan polymer used in the ophthalmic emulsion.

The present invention is partly based on the discovery that an increased concentration of the mucoadhesive galactomannan polymer in the ophthalmic emulsion can improve hydration protection against desiccation and protection by ocular surface hydration retention while maintaining the homogeneity of the phospholipid and oils in the ophthalmic emulsion.

It is well known that a tear film consists of three layers, which from posterior to anterior are the mucus layer, aqueous layer and lipid or oily layer. The mucus layer is the innermost and thinnest stratum of the tear film. It consists of mucin secreted by conjunctival goblet cells and glands of Manz, and converts the hydrophobic corneal surface into hydrophilic one. The intermediate aqueous layer forms the bulk of the tear film and consists of tears secreted by the main and accessory lacrimal glands. The lipid or oily layer is the outermost layer of tear film and is formed at the air-tear interface from the secretions of the Meibomian, Zeis, and Moll glands. This layer prevents the overflow of tears, retards their evaporation and lubricates the eyelids as they slide over the ocular surface.

Based on the knowledge of the tear film outer layer containing lipids, a person skilled in the art would increase the concentration of lipids and/or oils rather than the concentration of the mucoadhesive galactomannan polymer in the ophthalmic emulsion in order to increase both the hydration protection against desiccation and the surface hydration retention.

The present invention is also partly based on the discovery that an increased concentration of the mucoadhesive galactomannan polymer in the ophthalmic emulsion can increase polymer filament break up time. These data suggest that in-eye film stability would be greater during the blink interval than the comparators.

The present invention is further partly based on the discovery that decreased sized oil droplets allow for increases in the concentration of the mucoadhesive galactomannan polymer in the ophthalmic emulsion and also make the ophthalmic emulsion less opaque which reduces blurring upon instillation.

The present invention is related to a lipid-based ophthalmic oil-in-water emulsion wherein the ophthalmic emulsion has an oil droplet size that is very small. The ophthalmic emulsion will typically be aqueous and include a substantial amount of water. The ophthalmic emulsion will also typically include an anionic phospholipid, a hydrophilic surfactant (high HLB) and a hydrophobic (low HLB) surfactant. Further, the ophthalmic emulsion will typically include one or more mucoadhesive ingredients (e.g., galactomannan polymers) to aid in maintaining the emulsion on the corneal surface of the eye and/or aid in delivering one or more lipophilic compounds to the corneal surface. The ophthalmic emulsions of the present invention are most desirably used for dry eye therapeutics. However, without limitation, it is also contemplated that the ophthalmic emulsions may be used for drug delivery, vitamin delivery, botanical delivery, contact lens wetting and contact lens lubrication.

Unless otherwise specifically stated all emulsion ingredient amounts or percentages are weight volume percentages (w/v %).

The oil of the emulsion is dispersed throughout the continuous water or aqueous phase as small droplets that are substantially distinct and separate. It should be understood that, as used herein, the phase distinct and separate means that, at any give point in time, the droplets are distinct and separate. However, the droplets of the emulsion can combine and separate over time while maintaining a small droplet size distribution. The droplets of the emulsion of the present invention typically have a droplet size $D_{90}$ diameter no greater than about 700 nanometers (nm), more typically no greater than about 500 nm and still more typically no greater than about 300 nm. These droplets also typically have a droplet size $D_{90}$ diameter that is typically at least 10 nm, more typically at least 30 nm and still more typically at least 50 nm.

Particle or droplet size analyzers may be used to determine emulsion oil droplet size. For example, a Microtrac S3500 Particle Size Analyzer (Software Version 10.3.1) is a tri-laser particle size analyzer that can be used to measure emulsion oil droplet size. That particular analyzer measures laser light diffracted (scattered) from particles (e.g., droplets) in a flowing stream. The intensity and direction of the scattered light is measured by two optical detectors. Mathematical analysis of the diffraction pattern by the software generates a volume distribution of droplet size. The droplet diameter corresponding to 90% of the cumulative undersize distribution by volume is used.

The emulsion of the present invention is an oil-in-water emulsion. The oil can be any of numerous mineral, vegetable, and synthetic substances and/or animal and vegetable fats or any combination of oils. The oil can be soluble in various organic solvents such as ether but not in water. The oil phase can comprise, if desired a liquid hydrocarbon, such as a mineral oil, paraffin oils, petrolatum or hydrocarbon oils. Mineral oil is particularly preferred. A silicone oil may also be used. The oil phase can additionally include a waxy hydrocarbon, such as paraffin waxes, hydrogenated castor oil, Synchrowax HRC, Carnabau, beeswax, modified beeswaxes, microcrystalline waxes, and polyethylene waxes. The oil is typically at least 0.01 w/v %, more typically at least 0.1 w/v % and even more typically 0.8 w/v % of the emulsion. The oil is also typically no greater than about 20 w/v %, more typically no greater than about 5 w/v % and even more typically no greater than about 3 or even 1.5 w/v % of the emulsion The emulsion of the present invention also typically incorporates two or more surfactants, which act as emulsifiers aiding in the emulsification of the emulsion. Typically, these surfactants are non-ionic. The concentration of emulsifying surfactant in the emulsion is often selected in the range of from 0.1 to 10% w/v, and in many instances from 0.5 to 5% w/v. It is preferred to select at least one emulsifier/surfactant which is hydrophilic and has an HLB value of at least 8 and often at least 10 (e.g., 10 to 18). It is further preferred to select at least one emulsifier/surfactant which is hydrophobic and has an HLB value of below 8 and particularly from 1 to 6. By employing the two surfactants/emulsifiers together in appropriate ratios, it is readily feasible to attain a weighted average HLB value that promotes the formation of an emulsion. For most emulsions according to the present invention, the average HLB value is chosen in the range of about 6 to 12, and for many from 7 to 11.

For example, the HLB values for exemplary surfactants and mineral oil are as follows: hydrophobic surfactant (2.1), hydrophilic surfactant (16.9) and mineral oil (10.5). The concentrations of hydrophobic surfactant and hydrophilic surfactant used in exemplary emulsions were 0.38% and 0.29% based on these calculations.

$$.29/.67 = 0.43 \text{ and } .38/.67 = 0.57$$

$$\begin{aligned}
\text{hydrophobic surfactant} \quad & 2.1 \times 0.43 = 0.90 \\
\text{hydrophilic surfactant} \quad & 16.9 \times 0.57 = \underline{9.63} \\
& \phantom{16.9 \times 0.57 = }10.53
\end{aligned}$$

The ratio between hydrophobic surfactant and hydrophilic surfactant is equal to 1.32 which can be used to select the proper ratio of concentrations to be used for the two surfactants. The concentrations of hydrophobic surfactant and hydrophilic surfactant used in exemplary emulsions were 0.38% and 0.29% based on these calculations.

The hydrophilic surfactant is typically present in the emulsion in an amount that is at least about 0.01 w/v %, more typically at least about 0.08 w/v % and even more typically at least about 0.14 w/v %. The hydrophilic surfactant is typically present in the emulsion in an amount that is no greater than about 1.5 w/v %, more typically no greater than about 0.8 w/v % and even more typically no greater than about 0.44 w/v %.

The hydrophilic surfactant can be a fatty acid, an ester, an ether, an acid or any combination thereof. The hydrophilic surfactant may be ionic or non-ionic, but is preferably non-ionic. Many suitable surfactants/emulsifiers are non-ionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. Examples of hydrophilic surfactants/emulsifiers include ceteareth-10 to-25, ceteth-10-25, steareth-10-25, and PEG-15-25 stearate or distearate. Other suitable examples include C10-C20 fatty acid mono, di or tri-glycerides. Further examples include C18-C22 fatty alcohol ethers of polyethylene oxides (8 to 12 EO). One particularly preferred hydrophilic surfactant is polyoxyethylene-40-stearate, which is sold under the tradename MYRJ-52, which is commercially available from Nikko Chemicals.

The hydrophobic surfactant is typically present in the emulsion in an amount that is at least about 0.01 w/v %, more typically at least about 0.11 w/v % and even more typically at least about 0.16 w/v %. The hydrophobic surfactant is typically present in the emulsion in an amount that is no greater than about 10.0 w/v %, more typically no greater than about 2.0 w/v % and even more typically no greater than about 0.62 w/v %.

The hydrophobic surfactant can be a fatty acid, an ester, an ether, an acid or any combination thereof. The hydrophobic surfactant may be ionic or non-ionic, but is preferably non-ionic. The hydrophobic surfactant will typically include a hydrophobic moiety. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of hydrophobic surfactants include, without limitation, sorbitan fatty acid esters such as sorbitan monoleate, sorbitan monostearate, sorbitan monolaurate, sorbitan monopalmitate, sorbitan monoisostearate, sorbitan trioleate, sorbitan tristearate, sorbitan sesquioleate, sorbitan sesquistearate, combinations thereof or the like. One particularly preferred hydrophobic surfactant is a sorbitan tristearate sold under the tradename SPAN-65, which is commercially available from Croda Worldwide.

The types of galactomannans that may be used in the present invention are typically derived from guar gum, locust bean gum and tara gum. As used herein, the term "galactomannan" refers to polysaccharides derived from the above natural gums or similar natural or synthetic gums containing mannose or galactose moieties, or both groups, as the main structural components. Preferred galactomannans of the present invention are made up of linear chains of (1-4)-.beta.-D-mannopyranosyl units with .alpha.-D-galactopyranosyl units attached by (1-6) linkages. With the preferred galactomannans, the ratio of D-galactose to D-mannose varies, but generally will be from about 1:2 to 1:4. Galactomannans having a D-galactose: D-mannose ratio of about 1:2 are most preferred. Additionally, other chemically modified variations of the polysaccharides are also included in the "galactomannan" definition. For example, hydroxyethyl, hydroxypropyl and carboxymethylhydroxypropyl substitutions may be made to the galactomannans of the present invention. Non-ionic variations to the galactomannans, such as those containing alkoxy and alkyl (C1-C6) groups are particularly preferred when a soft gel is desired (e.g., hydroxylpropyl substitutions). Substitutions in the non-cis hydroxyl positions are most preferred. An example of non-ionic substitution of a galactomannan of the present invention is hydroxypropyl guar, with a molar substitution of about 0.4. Anionic substitutions may also be made to the galactomannans. Anionic substitution is particularly preferred when strongly responsive gels are desired. A galactomannan is typically present in a formulation of the present invention at a concentration of at least about 0.1 w/v %, more typically at least about 0.12 w/v % and even more typically at least about 0.14 w/v %, but typically no greater than about 0.5 w/v %, more typically no greater than about 0.4 w/v %, still more typically no greater than about 0.3 w/v %, and in other embodiments no greater than about 0.2 w/v %. Preferred galactomannans of the present invention are guar and hydroxypropyl guar.

The emulsion may include additional or alternative polymeric ingredients and/or viscosity agents. Examples include, without limitation, carboxymethylcellulose, hydroxypropylmethyl cellulose, hydroxyethyl cellulose, carboxyvinyl polymer, xanthan gum, hyaluronic acid, any combinations thereof or the like.

The emulsion of the present invention includes at least one phospholipid for aiding in maintaining the stability of the emulsion and for reducing droplet size of the oil. It is known that complex phospholipids can contain a polar group at one end of their molecular structure and a non-polar group at the opposite end of their molecular structure. A discussion of phospholipids can be found in Lehninger, Biochemistry, 2 ed., Worth Publishers, New York, pp. 279-306, incorporated herein by reference for all purposes.

Many complex phospholipids are known to the art. They differ in size, shape and the electric charge of their polar head groups. Phosphoglycerides are compounds where one primary hydroxyl group of glycerol is esterified to phosphoric acid, and the other two hydroxyl groups are esterified with fatty acids. The parent compound of the series is, therefore, the phosphoric acid ester of glycerol. This compound has an asymmetric carbon atom and, therefore, the term phosphoglycerides includes stereoisomers. All phosphoglycerides have a negative charge at the phosphate group at pH 7, and the $pK_a$ of this group is in the range of 1 to 2. The head groups of phosphatidylinositol, phosphatidylglycerol including diphosphatidylglycerols (having the common name cardiolipins) and the phosphatidylsugars have no electric charge, and all are polar because of their high hydroxyl group content. Because of the negative charge of the phosphate group and the absence of a charge in the head group, the net charge of each of these materials is negative, and these materials are within the scope of the invention. Suitable phospholipids are those carrying a net positive or negative charge under conditions of use. The preferred materials are those carrying a net negative charge because the negatively charged material will be repelled by the negatively charged ocular surface thereby permitting the maintenance of a relatively thick aqueous layer upon application to the eye. The most preferred phospholipid is an anionic phospholipid named dimyristoyl phosphatidylglycerol (DMPG), which is a polyol with a net negative charge. Phosphatidylglycerol or a phosphatidylinositol are other examples. Suitable phospholipid additives are disclosed in the above cited U.S. Pat. No. 4,914,088, which is fully incorporated herein by reference for all purposes.

Most phospholipids are water insoluble. However, for application to the eye, it is desirable that the phospholipid be homogeneously distributed throughout an aqueous medium. For those few phospholipids having a solubility within a useful concentration range for use as a treatment composition, a simple aqueous solution of the phospholipid in saline is satisfactory. For those phospholipids that are essentially water insoluble, an aqueous composition in the form of an emulsion may be used. An emulsion provides a treatment composition where the phase containing the phospholipid component is homogeneously distributed throughout the aqueous vehicle.

The concentration of the phospholipid in the treatment composition may vary within wide limits. A treatment composition containing the complex phospholipid in an amount as low as 0.01 weight percent provides some benefit. When the treatment composition is in the form of an emulsion, compositions containing the phospholipid in elevated concentrations approaching collapse of the emulsion into separate aqueous and phospholipid phases is possible. A clinically practical concentration range for the phospholipid in its vehicle varies from about 0.1 to 7.0 w/v % phospholipid by weight, and more preferably varies from about 0.1 and 5.0 w/v %. It should be noted that the most desired concentration for the phospholipid in the aqueous composition will vary from subject to subject.

Other additives may be present in the phospholipid treatment composition including neutral lipids such as one or more triglycerides, cholesterol esters, the natural waxes and cholesterol; higher molecular weight isoprenoids; stabilizers; preservatives; pH adjustors to provide a composition preferably having a pH between about 6 and 8 and more preferably between about 7.0 and 7.4; salt in sufficient concentration to form an isotonic composition; medicants; etc.

As indicated above, the emulsions of the present invention can include borate or borate/polyol buffer systems. As used herein, the term "borate" includes boric acid, salts of boric acid, other pharmaceutically acceptable borates, and combinations thereof. The following borates are particularly preferred: boric acid, sodium borate, potassium borate, calcium borate, magnesium borate, manganese borate, and other such borate salts.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol and sorbitol. Especially preferred polyols are mannitol and sorbitol; most preferred is sorbitol.

The use of borate-polyol complexes in ophthalmic compositions is described in U.S. Pat. No. 6,503,497 (Chowhan); the entire contents of which are hereby incorporated in the present specification by reference. The emulsions of the present invention preferably contain one or more borates in a concentration that is at least about 0.01% w/v, more typically at least about 0.3% w/v and even more typically at least about 0.8% w/v, but typically no greater than about 5.0% w/v, more typically no greater than about 2.0% w/v and even more typically no greater than about 1.2% w/v. It is generally desirable for the amount of the one or more borates to be sufficient to allow the formation of borate/polyol complexes and, when desired, to aid in gelling the galactomannan polymer upon application of the emulsion to the eye.

The compositions of the present invention typically include a preservative. Potential preservatives include, without limitation, hydrogen peroxide, chlorine containing preservatives such as benzalkonium chloride or others. According to a preferred aspect, however, the ophthalmic emulsion of the present invention is substantially free of benzalkonium chloride. Most preferred preservatives included in the ophthalmic composition are polymeric quaternary ammonium compounds.

As used herein, the phrase "substantially free of" as it refers to an ingredient of the ophthalmic composition means that it is contemplated that the ophthalmic solution can be either entirely devoid of that particular ingredient or includes only a nominal amount of that particular ingredient.

The polymeric quaternary ammonium compounds useful in the compositions of the present invention are those which have an antimicrobial effect and which are ophthalmic ally acceptable. Preferred compounds of this type are described in U.S. Pat. Nos. 3,931,319; 4,027,020; 4,407,791; 4,525, 346; 4,836,986; 5,037,647 and 5,300,287; and PCT application WO 91/09523 (Dziabo et al.). The most preferred polymeric ammonium compound is polyquaternium 1, otherwise known as POLYQUAD® or ONAMERM® with a number average molecular weight between 2,000 to 30,000. Preferably, the number average molecular weight is between 3,000 to 14,000.

The polymeric quaternary ammonium compounds are generally used in the compositions of the present invention in an amount that is greater than about 0.00001 w/v %, more typically greater than about 0.0003 w/v % and even more typically greater than about 0.0007 w/v % of the ophthalmic composition. Moreover, the polymeric quaternary ammonium compounds are generally used in the compositions of the present invention in an amount that is less than about 3 w/v %, more typically less than about 0.003 w/v % and even more typically less than about 0.0015 w/v % of the ophthalmic composition.

The emulsion of the present invention can include any of a multitude of ophthalmic therapeutic agents. Non-limiting examples of potential ophthalmic therapeutic agents for the present invention include: anti-glaucoma agents, anti-angiogenesis agents; anti-infective agents; anti-inflammatory agents; growth factors; immunosuppressant agents; and anti-allergic agents. Anti-glaucoma agents include beta-blockers, such as betaxolol and levobetaxolol; carbonic anhydrase inhibitors, such as brinzolamide and dorzolamide; prostaglandins, such as travoprost, bimatoprost, and latanoprost; seretonergics; muscarinics; dopaminergic agonists. Anti-angiogenesis agents include anecortave acetate (RE-TAANE™, Alcon™ Laboratories, Inc. of Fort Worth, Tex.) and receptor tyrosine kinase inhibitors (RTKi). Anti-inflammatory agents include non-steroidal and steroidal anti-inflammatory agents, such as triamcinolone actinide, suprofen, diclofenac, ketorolac, nepafenac, rimexolone, and tetrahydrocortisol. Growth factors include EGF or VEGF. Anti-allergic agents include olopatadine and epinastine. The ophthalmic drug may be present in the form of a pharmaceutically acceptable salt.

The present invention can be particularly useful for delivery therapeutic agents that relieve symptoms of dry eye conditions. Examples include, without limitation, steroidal and/or non-steroidal anti-inflammatory agents; selective PDE IV inhibitors such as cilomilast, cyclosporins, combinations thereof or the like. The emulsion of the invention can also be used in other fields, such as to deliver cooling agents, deliver antioxidants (omega-3 and omega-6 fatty acids) and other bioactives for ophthalmic uses. For example, nutriceuticals such as vitamin A (retinol), vitamin D (calciferol), vitamin E, tocopherols, vitamin K (quinone), beta-carotene (pro-vitamin-A) and combinations thereof.

Generally, amounts of therapeutic agent, when used, can be quite variable depending upon the agent or agents used. As such, the concentration of therapeutic agent can be at least about 0.005 w/v %, more typically at least about 0.01 w/v % and even more typically at least about 0.1 w/v %, but typically no greater than about 10 w/v %, more typically no greater than about 4.0 w/v %, still more typically no greater than about 2.0 w/v %.

The emulsions of the present invention may optionally comprise one or more additional excipients and/or one or more additional active ingredients. Excipients potentially used in the ophthalmic emulsions include, but are not limited to, demulcents, tonicity agents, preservatives, chelating agents, buffering agents, and surfactants. Other excipients comprise solubilizing agents, stabilizing agents, comfort-enhancing agents, polymers, emollients, pH-adjusting agents and/or lubricants.

The emulsion is typically aqueous and therefore includes a substantial amount of water, which is typically purified. The emulsion typically includes water at a concentration of at least about 50 w/v %, more typically at least about 85 w/v % and even more typically at least about 93 w/v %, but typically no greater than about 99.99 w/v %, more typically no greater than about 99.0 w/v %, still more typically no greater than about 0.3 w/v % and even still more typically no greater than about 98 w/v %.

The emulsion of the present invention may be formed using a variety of combining and mixing protocol and techniques known to those skilled in the art. According to one preferred embodiment, however, the ingredients are mixed and combined according to a specific protocol. In such protocol, multiple admixtures are formed and those admixtures are combined to form the emulsion. The first admixture is formed by mixing the oil and the surfactants at an elevated temperature to form an oil phase admixture. The second admixture is formed mixing the anionic phospholipid into purified water at an elevated temperature to form a water phase admixture. Thereafter, the oil phase admixture and the water phase admixture are mixed at an elevated temperature and subsequently homogenized using a homogenizer to form an initial emulsion. A third admixture is formed by mixing the galactomannan polymer with water and adjusting pH as needed to form a galactomannan polymer slurry. The galactomannan polymer slurry is then mixed with initial emulsion and form a polymer enhanced emulsion. A fourth admixture is formed by mixing any combination of the following to form a salt solution: borate, polyol, preservative and any other ingredients. The salt solution and the enhanced emulsion are then mixed followed by the addition of a sufficient quantity (Q.S.) of water and pH adjustment.

The emulsion can be used as an ocular lubricant, a drug delivery vehicle or the like. However, it has been found particularly desirable for use as a dry eye therapy. As such, an individual diagnosed with or experiencing dry eye symptoms can dispense the emulsion to that individual's eye for alleviating those dry eye symptoms. Typically the emulsion is provided in an eye dropper such that an individual may instill one, two or more drops into one or both of their eyes on a regular or as needed basis. Upon instillation, the emulsion will typically gel upon the corneal surface of the eye allowing for more significant therapeutic effects such as aiding in the delivery of lipids to the ocular surface.

Advantageously, the stability of the oil in water emulsion of the present invention can facilitate lubrication and/or the delivery of lipids (e.g., lipid therapeutic agents) to the ocular surface. These lipids can aid in stabilizing the tear film and/or can provide alternative therapeutic advantages to the eye. Moreover, the mucoadhesive polymer can aid residence time of the emulsions upon the eye such that the emulsions can be more efficacious.

Formulations

The invention emulsion formulation included: HP-guar, boric acid, propylene glycol (demulcent), disodium edetate, sorbitol and polyquad (preservative) in the aqueous phase, and mineral oil, anionic phospholipid (dimyristoyl phosphatidylglycerol) and sorbitan tristearate and polyoxyl 40 stearate (emulsifying agents) in the oil phase. The emulsion of the present invention (denoted HP-Guar emulsion) and the comparator emulsion (denoted SYSB emulsion) have the same general composition but differ in terms of the droplet size, and in the concentration of HP-guar as illustrated in Table 1.

TABLE 1

| COMPONENT | CONCENTRATION PERCENT, W/V (HP-Guar Invention) | CONCENTRATION PERCENT, W/V (SYSB comparator) |
| --- | --- | --- |
| Polyquaternium-1 | 0.001 + 10%* | 0.001 + 10%* |
| HP-Guar | 0.15 | 0.05 |
| Mineral oil | 1.0 | 1.0 |
| Boric Acid | 1.0 | 1.0 |
| Anionic Phospholipid | 0.005 | 0.005 |
| Polyoxyl 40 Stearate | 0.38 | 0.38 |
| Sorbitan Tristearate | 0.29 | 0.29 |
| Propylene Glycol | 0.6 | 0.6 |
| Sorbitol | 0.7 | 0.7 |
| Edetate Disodium | 0.025 | 0.025 |
| Sodium Hydroxide | Adjust pH to 7.0 | Adjust pH to 7.0 |
| Hydrochloric Acid | Adjust pH to 7.0 | Adjust pH to 7.0 |
| Purified Water | QS 100 | QS 100 |
| Hydrochloric Acid | Adjust pH to 7.0 | Adjust pH to 7.0 |
| Purified Water | QS 100 | QS 100 |
| Desiccation Protection (%) | 39.5 ± 14.6 | 7.1 ± 10.0 |
| Retention Protection (%) | 32.6 ± 13.6 | 11.0 ± 8.5 |

Table 1 above shows one formulation for example of HP-guar emulsion in accordance with the present invention and the formulation of the SYSB comparator emulsion. Comparing to SYSB comparator, the HP-Guar emulsion has a decrease in $D_{90}$ droplet size from 480 nm to 150 nm by using a high pressure homogenizer. A reduction in droplet size allows increases in the HP-Guar concentration while maintaining good physical stability.

TABLE 2

| Components | Typical Concentration range for testing |
| --- | --- |
| Polyquaternium-1 | 0-0.001% |
| Mineral Oil | 1 |
| HP-Guar | 0.15-0.5 |
| polyoxyl-40 stearate | 0.19-0.38 |
| Sorbitan tristearate | 0.15-0.29 |
| Anionic Phospholipid | 0-0.1 |
| Boric Acid | 1.0 |
| Sorbitol | 0.7 |
| Propylene Glycol | 0.6 |
| $ZnCl_2$ | 0-0.0015 |

Table 2 above shows a typical concentration range in accordance with the present invention.

Material and Methods

Cell Hydration and Surface Retention Assay

Monolayer FTT (14-3-3) human corneal epithelial (HCE) cells were grown to confluence on collagen IV coated 48-well plates in EpiLife® medium containing calcium and supplemented with human corneal growth supplement for 48 hours. Cells were then incubated with 150 µL test formulation (HP-guar emulsion, SYSB or vehicle) for 30 minutes at 37° C. To measure the cell hydration protection against desiccation, the test formulations were removed gently, and the cells were desiccated at 37° C. and 45% relative humidity for 30 minutes. To measure the hydration retention after desiccation, the test formulations were removed gently and the cells were rinsed three times with media (EpiLife® medium with calcium) and then desiccated as described above.

After desiccation, cell viability was measured using MTS assay (Promega, Madison, Wis., USA). The % viability was calculated relative to the undesiccated media control (Absorbance of test sample/Absorbance of the undesiccated media control×100). The protection (%) was calculated as the viability of the test formulation relative to the desiccated media control (% viability of the test sample–% viability of the desiccated media control).

Elastic Filament Strength

An extensional rheometer, HAAKE CaBER1 (Thermo Scientific) was used to characterize the polymer filament break-up time (PFBUT) of each test formulation. The test formulation was loaded between two plates of the rheometer. The top plate was extended to a distance of 8.00 mm, the average distance between an upper and lower eyelid. A high precision laser micrometer was used to measure the diameter of the thinning filament as a function of time. The time taken for the formulation to break between the two plates was recorded as the PFBUT.

Results:

Cell Hydration Retention and Hydration Protection:

HP-guar emulsion demonstrated significantly greater hydration protection after desiccation compared with SYSB comparator. The % cell viability (mean±SD) after desication in cultured HCE cells pretreated with test formulations was 39.5±14.6 (sample size, n=33) with HP-guar emulsion of the present invention, 7.1±10.0 (with sample size, n=63) SYSB comparator (FIG. 1). The % cell viability (mean±SD) after desication in cultured HCE cells pretreated with desiccated media control (the same formulation as HP-guar emulsion without any HP-guar emulsion) was −0.1±0.9 (sample size, n=38).

Figure 2:
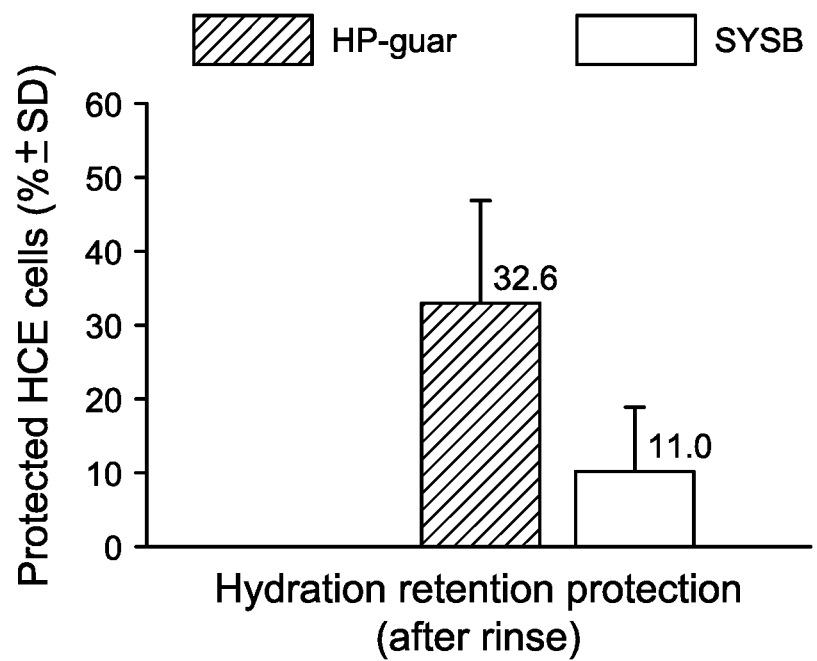
FIG. 2 is a bar chart comparing retention performance of a composition comprising 0.05% hydroxypropyl guar and 0.15% hydroxypropyl guar.

Protection by hydration retention against desiccation after rinsing of formulations was also significantly greater with HP-guar emulsion of the present invention compared with SYSB comparator and numerically higher in HP-guar emulsion treated cells when compared with SYSB comparator (FIG. 2). The % cell viability after rinse was 32.6±13.6 (sample size, n=33), 11.0±8.5 (with sample size, n=63) in samples pretreated with HP-guar emulsion of the present invention and SYSB comparator, respectively. The % cell viability after rinse for desiccated media control (the same formulation as HP-guar emulsion without any HP-guar emulsion) was 1.2±0.6 (sample size, n=63).

Corneal epithelial cells treated with the HP-guar emulsion of the present invention demonstrated increased hydration protection and retention against desiccation relative to SYSB comparator. The desiccation protection was about 3-fold higher with HP-guar emulsion of the present invention relative to SYSB comparator, indicating that the HP-guar emulsion formulation of the present invention also provides longer moisture retention and hydration-effect than the SYSB comparator.

Figure 3:
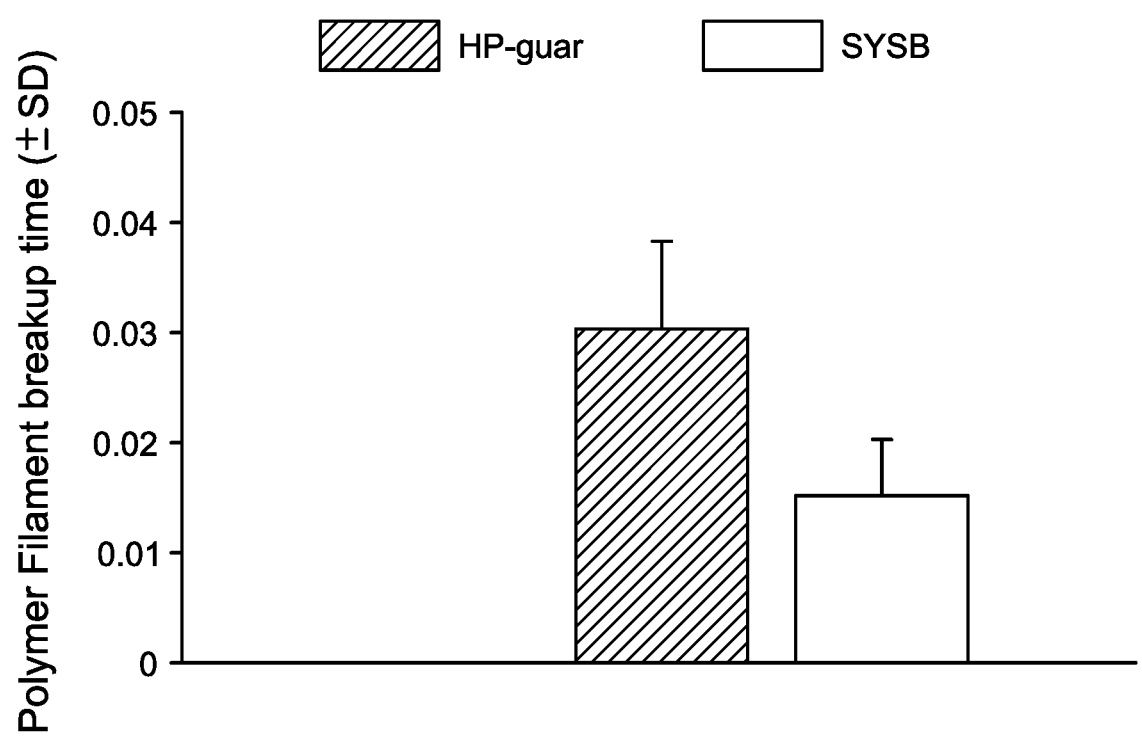
FIG. 3 is a bar chart comparing polymer filament break-up time performance of a composition comprising 0.05% hydroxypropyl guar and 0.15% hydroxypropyl guar.

Elastic Filament strength:

The HP-guar emulsion of the present invention showed significant increase in elastic filament strength compared to SYSB comparator formulation (p<0.05). The PFBUT (mean±SD) at shear rate $10^{-1}5$ was 0.031±0.008 s for the HP-guar emulsion of the present invention, 0.016±0.005 s for SYSB comparator (FIG. 3). The PFBUT (mean±SD) at shear rate $10^{-1}5$ for was media control (the same formulation as HP-guar emulsion without any HP-guar emulsion) was 0.017±0.001 s.

The results demonstrate that the HP-guar emulsion formulation of the present invention and the SYSB comparator have a Filament Break up Time of 0.031 sec and 0.016 sec respectively and the difference is statically significant (p<0.05). Therefore, application of the HP-guar emulsion formulation of the present invention should allow patients with evaporative dry eye disease to reduce the rate of tear evaporation. Furthermore, application of the HP-guar emulsion formulation of the present invention should also allow patients with aqueous-deficient dry eye disease having low tear volume due to underproduction of aqueous component to sufficiently hydrate the ocular surface.

We claim:

1. An ophthalmic emulsion, the emulsion comprising:
water forming an aqueous phase;
oil forming an oil phase;
a hydrophilic surfactant having an HLB value from 10 to 18;
a hydrophobic surfactant having an HLB value from 1 to 6;
a charged phospholipid;
borate; and
a mucoadhesive galactomannan polymer;
wherein the mucoadhesive galactomannan polymer is present in the emulsion at a concentration of at least about 0.1 w/v % but no greater than 0.5 w/v %;
wherein the ophthalmic emulsion has a hydration protection against desiccation of at least 10% higher than a control emulsion, wherein the control emulsion has the same composition of the ophthalmic emulsion except of containing 0.05 w/v % of the same galactomannan polymer used in the ophthalmic emulsion.

2. The emulsion as in claim 1 wherein the oil is a hydrocarbon selected from mineral oil, paraffin oil and petrolatum.

3. The emulsion as in claim 1 wherein the oil is at least 0.1 w/v % and no greater than 3 w/v % of the emulsion.

4. The emulsion as in claim 3 wherein the hydrophilic surfactant is present in the emulsion in an amount that is at least 0.08 w/v % and is no greater than about 0.8 w/v %.

5. The emulsion as in claim 4 wherein the hydrophilic surfactant is polyoxyethylene-40-stearate.

6. The emulsion as in claim 4 wherein the hydrophobic surfactant is at least about 0.01 w/v % and is no greater than 2.0 w/v %.

7. The emulsion as in claim 6 wherein the hydrophobic surfactant is a sorbitan tristearate.

8. The emulsion as in claim 1 wherein the mucoadhesive galactomannan polymer is selected from the group consisting of guar and hydroxypropyl guar.

9. The emulsion as in claim 8 wherein the mucoadhesive galactomannan polymer is present in the emulsion at a concentration of at least about 0.12 w/v % but no greater than 0.4 w/v %.

10. The emulsion as in claim 8 wherein the charged phospholipid is an anionic phospholipid named dimyristoyl phosphatidylglycerol.

11. The emulsion as claim 10 wherein the phospholipid is present in the emulsion in a concentration from about 0.13 to 0.3 percent by weight.

12. The emulsion as in claim 1 further comprising a borate/polyol buffer system.

13. The emulsion as in claim 12 wherein the preservative is a polymeric quaternary ammonium compound.

14. The emulsion as in claim 1, wherein:
i. the oil phase is in droplets within the aqueous phase and the droplets have a $D_{90}$ diameter that is no greater than about 700 nm but is at least 10 nm; and
ii. the borate and galactomannan polymer cooperatively act to form a gel upon instillation of the emulsion in an eye of an individual.

15. The emulsion as in claim 14, wherein the oil phase is in droplets within the aqueous phase and the droplets have a $D_{90}$ diameter that is no greater than about 500 nm but is at least 30 nm.

16. The emulsion as in claim 15, wherein the oil phase is in droplets within the aqueous phase and the droplets have a $D_{90}$ diameter that is no greater than about 300 nm but is at least 50 nm.

* * * * *